United States Patent [19]

Fukasawa et al.

[11] Patent Number: 4,987,241
[45] Date of Patent: Jan. 22, 1991

[54] POLYALUMINUM DIALKYL PHOSPHATE, OIL GELLING AGENT COMPRISING THE SAME, AND COMPOSITION FOR EXTERNAL APPLICATION COMPRISING THE SAME

[75] Inventors: Junichi Fukasawa, Yokohama; Noriko Shirakawa, Kawasaki; Hisao Tsutsumi, Saitama, all of Japan

[73] Assignee: Kao Corporation, Tokyo, Japan

[21] Appl. No.: 301,120

[22] Filed: Jan. 25, 1989

[30] Foreign Application Priority Data

Jan. 29, 1988 [JP]  Japan ................................ 63-19094

[51] Int. Cl.$^5$ .............................................. C07F 9/02
[52] U.S. Cl. .................................................... 556/174
[58] Field of Search ........................................ 586/174

[56] References Cited

U.S. PATENT DOCUMENTS

| 4,163,018 | 7/1979 | Tada et al. ............ 556/176 X |
| 4,206,133 | 6/1980 | Joyce et al. ........... 556/176 X |
| 4,226,908 | 10/1980 | Yoshino et al. ....... 556/176 X |
| 4,233,253 | 11/1980 | Hoff et al. ............ 556/176 X |
| 4,272,448 | 6/1981 | Bernard et al. ....... 516/174 |
| 4,465,516 | 8/1984 | Darmer et al. ........ 556/176 X |

FOREIGN PATENT DOCUMENTS

| 133702 | 3/1985 | European Pat. Off. ...... 556/174 UX |
| 1020013 | 11/1955 | Fed. Rep. of Germany ...... 556/174 UX |

Primary Examiner—Paul F. Shaver

Attorney, Agent, or Firm—Oblon, Spivak, McClelland, Maier & Neustadt

[57] ABSTRACT

A polyaluminum dialkyl phosphate is disclosed. The compound is prepared by the reaction of:
(A) a dialkyl phosphate represented by formula (I):

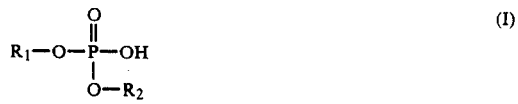

wherein $R_1$ and $R_2$ independently represent a hydrocarbon group of a $C_{8-26}$ carbon atom content, or a salt thereof, and
(B) a basic polyaluminum salt represented by formula (II):

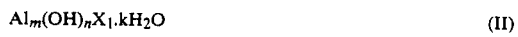

wherein X represents an anion having a valency of x other than a hydroxyl ion, m represents a positive integer satisfying the equation: $3m = n + x1$, and k represents 0 or a positive integer, in an aqueous medium in which the resulting polyaluminum dialkyl phosphate is insoluble. The polyaluminum dialkyl phosphate, when it is formulated into a liquid oil, provides a highly transparent, densely structure, soft gel which contains only small amount of free oil component. The gel possesses favorable rheological characteristics and can adequately disperse by a stress and imparts a good feeeling upon use.

1 Claim, 1 Drawing Sheet

POLYALUMINUM DIALKYL PHOSPHATE, OIL GELLING AGENT COMPRISING THE SAME, AND COMPOSITION FOR EXTERNAL APPLICATION COMPRISING THE SAME

BACKGROUND OF THE INVENTION

1. Field of the Invention

This invention relates to a novel polyaluminum dialkyl phosphate, an oil gelling agent comprising such a polyaluminum dialkyl phosphate, and a composition for external application comprising such a polyaluminum dialkyl phosphate which utilizes the characteristic features of such a such a polyaluminum dialkyl phosphate.

2. Description of the Background

Metallic soaps, fatty acid dextrin esters, metallic salts of dialkyl phosphate, organic-denatured bentonites, or the like have been used, because of their gelling capabilities as a gelling agent for medicines and cosmetics, an water-in-oil (w/o) type emulsion stabilizer, a pigment dispersing agent for cosmetics and paint, paint flowpreventives, and the like.

These metallic soaps, fatty acid dextrin esters, and metallic salts of dialkyl phosphate, however, when heated and dissolved into an oil and then cooled to a temperature below the phase inversion point (Tc) of the system, cause the system to become a brittle, solid gel. If a stress is applied to this gel, the material is deformed and can not restore its original shape. It must be heated to a temperature above Tc in order to restore the original shape. Because of this, those compounds having a branched, long alkyl group in their molecule and a Tc below a room temperature are used. These compounds, however, produce a gel which is too viscous. Such a gel is cobwebby (draws filaments), providing inconvenience and unacceptable feeing to the users.

Organic-denatured bentonites have, therefore, been used as a gelling agent for providing thixotropic rheological characteristics to oils. Organic-denatured bentonites, however, are produced through intercalation of an alkyl amine on montmorillonite which is a clay mineral. This poses a problem in view of safety of alkyl amine when the material is used for medicines or cosmetics. Furthermore, the turbidity caused by an organic-denatured bentonite because of inclusion of montmorillonite sometimes affects the color of the composition to which this substance is formulated. For this reason the use of organic-denatured bentonites for compositions requiring a delicate color tone is not suitable. In addition, this gelling agent is dispersed in an oil with the aide, as a carrier, of a smectite layer which is a layer constituting montmorillonite and has a expansion of 0.1 to several microns. This tends to leave a large proportion of oil unwrapped and free, when the carrier disperses into oil and wraps the oil, preventing a dense and soft gel from being produced. Because of this the gelling agent only produces rough and unsoft gels.

There is, therefore, a strong need for the development of a gelling agent which can provide thixotropic rheological characteristics to oils, possesses a high degree of safety, is transparent, gives a good feeling to the users, and is free from cobweb (does not draw filaments).

In view of this situation, the present inventors have undertaken extensive studies, and as a result have found that a novel polyaluminum dialkyl phosphate can provide a gelling agent satisfying the above requirements.

SUMMARY OF THE INVENTION

Accordingly, an object of this invention is to provide a polyaluminum dialkyl phosphate which is prepared by the reaction of:

(A) a dialkyl phosphate represented by formula (I):

wherein $R_1$ and $R_2$ independently represent a hydrocarbon group of a $C_{8-26}$ carbon atom content, or a salt thereof, and (B) a basic polyaluminum salt represented by formula (II):

wherein X represents an anion having a valency of x other than a hydroxyl ion, m represents a positive integer satisfying the equation: $3m = n + xl$, and k represents 0 or a positive integer, in an aqueous medium in which the resulting polyaluminum dialkyl phosphate is insoluble.

Another object of this invention is to provide an oil gelling agent comprising such a polyaluminum dialkyl phosphate as well as a composition for external application containing such an oil gelling agent.

Other objects, features and advantages of the invention will hereinafter become more readily apparent from the following description.

DETAILED DESCRIPTION OF THE INVENTION AND PREFERRED EMBODIMENTS

Figure 1:
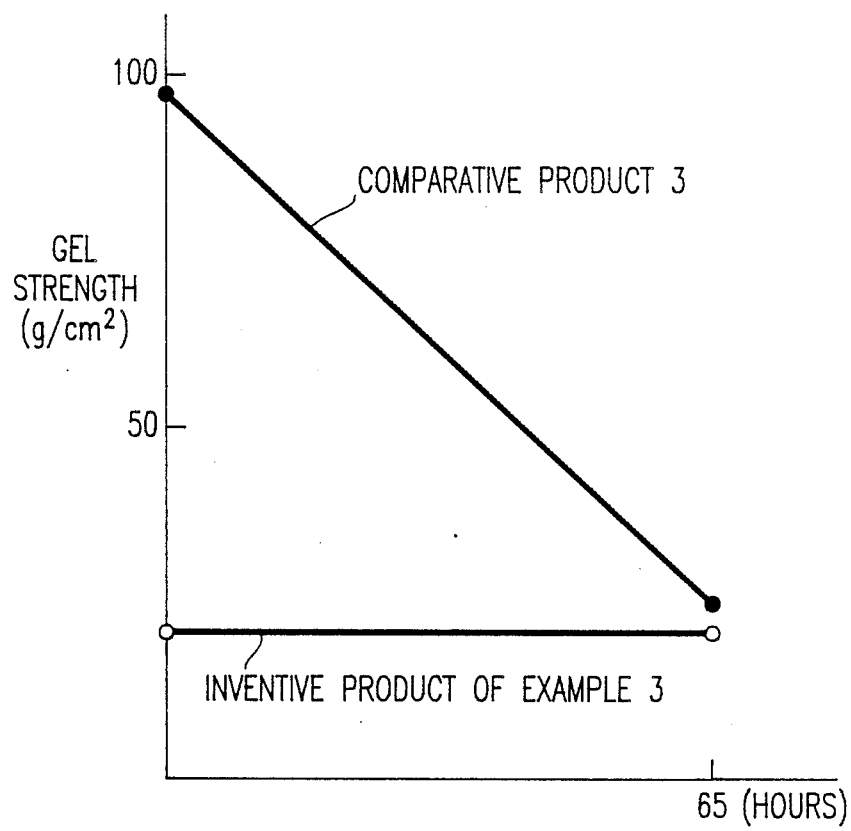
FIG. 1 is a drawing showing changes in gel-strength over time of gels prepared using polyaluminum dicetyl phosphate and aluminum tri(dicetyl)phosphate, as gelling agents.

In the present invention, the hydrocarbon group represented by $R_1$ and $R_2$ of formula (I) may be any hydrocarbon groups, including saturated or unsaturated, and linear or branched hydrocarbon groups. Particularly preferable hydrocarbon groups are saturated, linear hydrocarbon groups containing 12 to 20 carbon atoms. Those containing less than 8 carbon atoms, when made into a complex, cannot provide a sufficiently high viscosity to oils or fats. While, on the other hand, those containing more than 26 carbon atoms are not desirable because they do not dissolve in organic solvents. Given as examples of favorable hydrocarbon groups are octyl, nonyl, decyl, dodecyl, undecyl, tridecyl, tetradecyl, pentadecyl, haxadecyl, heptadecyl, octadecyl, nonadecyl, eicosyl, heneicosyl, docosyl, tricosyl, tetracosyl, pentacosyl, hexacosyl, decenyl, dodecenyl, undecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, octadienyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacosadienyl, hexacosadienyl, 2- hexyldecyl, 2-octylundecyl, 2-decyltetradecyl, and the like.

These dialkyl phosphates can be used as they are. It is desirable, however, in order to promote their dispersing abilities or solubilities into an aqueous medium, to covert them into salts of alkali metal such as sodium salt, potassium salt, or the like, salts of alkanolamine such as monoethanolamine salt, diethanolamine salt, or the like, or salts of basic amino acid such as salt of lysin, arginine, or the like.

The basic polyaluminum salt represented by formula (II) is a polynuclear ion formed through combination of a plurality of aluminum atoms in an aqueous medium. There are no specific restrictions as to the types of the counter ion X. The examples include halogen ions such as chlorine, bromine, and iodine, monovalent anions such as nitric acid, perchloric acid, and the like, bivalent anions such as sulfuric acid, and the like. Specific examples of the basic polyaluminum salt which can be used include $Al_2(OH)_5Cl$, $Al_3(OH)_3Cl_6$, $Al_{16}(OH)_{42}Cl_6$, $Al_3(OH)_3Br_6$, $Al_{16}(OH)_{42}Br_6$, $Al_3(OH)_3I_6$, $Al_{16}(OH)_{42}(SO_4)_3$, and the like. Although there are many factors still to be elucidated about the structure of the compounds represented by formula (II) in an aqueous medium, aluminum chlorohydrate having formula $Al_2(OH)_5 \cdot 2H_2O$, for example, is considered to exist in an aqueous solution as a polynuclear ion, in which 12 aluminum atoms encompass one aluminum atom, i.e., of formula $Al_{13}O_4(OH)_{24}(H_2O)7 + 12$ [Journal of the Society of Cosmetic Chemist, 33, 281–295 (1982)].

Polyaluminum dialkyl phosphate of this invention can be prepared by dissolving or suspending a dialkyl phosphate of formula (I), or preferably its salt, and a basic polyaluminum salt of formula (II), separately in an aqueous medium, and then mixing these solutions or suspensions together under heating.

Here, given as examples of an aqueous medium which can be used are mixed solvents of water and an organic solvent such as methanol, ethanol, acetone, or the like. Since, polyaluminum dialkyl phosphate of this invention can be obtained as a precipitate insoluble in these aqueous media, this precipitate is collected by filtration, and, if required, can be washed and dried.

Liquid oils to be gelled for use as a composition for external application include, for example, linear or branched hydrocarbons such as hexane, octane, decane, dodecane, terpenes, iso-paraffins, and the like; cyclic hydrocarbons such as squalane, squalene, and the like; aromatic hydrocarbons such as toluene, benzene, xylene, and the like; naturally occurring hydrocarbon mixtures such as petroleum ether, liquid paraffin, and the like; esters produced from a higher fatty acid such as isopropyl mirystate and a lower alcohol; esters produced from a lower fatty acid such as cetyl lectate and a higher alcohol; and the like. These liquid oils can be used independently or two or more of them can be used together. Among these liquid oils, nonpolar liquid oils such as hydrocarbons can produce a soft gel with a high degree of transparency and favorable thixotropic rheological characteristics.

Included in compositions for external application prepared using the gelling agent of this invention are pharmaceuticals, cosmetics, greases, paints, and the like. For the preparation of these products, beside liquid oils and gelling agents which are essential for such compositions, various optional components can be formulated. These optional components include, for example, solid oils, purified water, various kinds of surface active agents (for dispersing pigments), humectants, antiseptics, antioxidants, pharmaceutically active components, perfumes, powders, and the like.

When the component is to be used as a cosmetic, especially good results are obtained if this is used for make-up cosmetics such as foundations, etc. or skin-care cosmetics such as creams, oil gel cleanser, milky lotions, etc.

The composition for external application of this invention can be prepared by blending a polyaluminum dialkyl phosphate, a liquid oil, and any optional components under heating, and, if necessary, by filling the blend into a container.

When the polyaluminum dialkyl phosphate of this invention is used as a gelling agent, the preferable amount to be formulated is 2.5 to 25 % by weight, and particularly preferably 5 to 15% by weight, per the amount of oils to be used. Desirable formulations of compositions for external application in which the oil gelling agent of this invention is used are as follows:

| Component | Ointment | Cream | Foundation |
|---|---|---|---|
| Polyaluminum dialkyl phosphate | 2.5–25 | 0.2–10 | 0.2–10 |
| Liquid oil | 75–97.5 | 5–80 | 5–80 |
| Pigment | — | — | 2.5–25 |
| Water | — | 20–95 | 0–50 |
| Other components (Solid, semi-solid oils, etc.) | 0–20 | 0–20 | 0–50 |

Since dialkyl phosphate, which is the major component of polyaluminum dialkyl phosphate of this invention, has a high degree of stability, and basic polyaluminum, which acts as a carrier of the dialkyl phosphate, is very small in size, e.g. 50°–60° A, the polyaluminum dialkyl phosphate provides a highly transparent, densely structured, soft gel which contains only small amount of free oil component, when it is formulated into a liquid oil. A gel which is capable of drawing filaments has in its gel structure a fibrous structure which keeps each of the filaments strong enough to prevent itself from being cut by a stress. In the gel obtained using the polyaluminum dialkyl phosphate of this invention as an oil gelling agent, however, molecules of the gelling agent are not combined with each other at a very strong force, so that the polyaluminum dialkyl phosphate of the present invention can provide a creamy gel possessing favorable rheological characteristics, by which the gel can adequately disperse by a stress and imparts a good feeling upon use.

Other features of the invention will become apparent in the course of the following description of the exemplary embodiments which are given for illustration of the invention and are not intended to be limiting thereof.

EXAMPLES

Reference Example 1

Preparation of basic salt of polyaluminum: $Al_2(OH)_5Cl$

Into a 200 ml short-necked Kjeldahl flask 40 ml of purified water, 9.66 g (0.04 mol) of $AlCl_3 \cdot 6H_2O$ (molecular weight: 241.5), and 5.4 g (0.2 mol) of metallic aluminum were charged, and the mixture was stirred and heated to react under refluxing. After the completion of the reaction, the reaction mixture was filtered, and the filtrate was dried by means of a rotary evaporator.

Dried substance was pulverized to obtain a sample. The sample was white powders and was considered to have formula $Al_2(OH)_5Cl$ based on the materials used.

Reference Example 2

Preparation of basic salt of polyaluminum: $Al_2(OH)_7Cl_3$

Into a 200 ml short-necked Kjeldahl flask 40 ml of distilled water, 9.66 g (0.04 mol) of $AlCl_3 \cdot 6H_2O$ (molecular weight: 241.5), and 3.78 g (0.14 mol) of metallic aluminum were charged, and the mixture was stirred and heated to react under refluxing. After the completion of the reaction, the reaction mixture was filtered, and the filtrate was dried by means of a rotary evaporator. Dried substance was pulverized to obtain a sample. The sample thus obtained was white powders and was considered to have formula $Al_3(OH)_7Cl_2$ based on the materials used.

EXAMPLE 1

Preparation of polyaluminum dicetyl phosphate: $[Al_2(OH)_5Cl]$ 300 ml of ethanol was charged into a 1 liter beaker, and 50 g (0.092 mol) of dicetyl phosphate (molecular weight: 546) was dissolved into the ethanol at a temperature of 60 to 70° C. To the solution was added 10% aqueous solution of sodium hydroxide (equivalent of 0.092 mol NaOH) and the reaction was carried out while stirring. The reaction mixture, after having been allowed to stand at the ambient temperature, was filtered to collect the precipitate. The filtered precipitate was purified by recrystallization twice with methanol. The purified substance was dried at 50° C. for 6 hours.

Distilled water (800 ml) was heated to 60 to 70° C. to dissolve 15.9 g of the above reaction product. A solution of 5.804 g of basic salt of polyaluminum prepared in Reference Example 1 in 50 ml of distilled water was added to this solution of the reaction product. The mixture was stirred for 30 minutes at 60 to 70° C., and allowed to stand at the ambient temperature. A white precipitate produced was collected by filtration, washed thoroughly with distilled water, and recrystallized with methanol. The product thus produced was dried at 50° C. for 6 hours to obtain 16.5 g of a sample in a white powdery form.

EXAMPLE 2

Preparation of polyaluminum dicetyl phosphate: $[Al_3(OH)_7Cl_2]$ 300 ml of ethanol was charged into a 1 liter beaker, and 50 g (0.092 mol) of dicetyl phosphate (molecular weight: 546) was dissolved into the ethanol at a temperature of 60 to 70° C. To the solution was added 10% aqueous solution of sodium hydroxide (equivalent of 0.092 mol NaOH) and the reaction was carried out while stirring. The reaction mixture, after having been allowed to stand at the ambient temperature, was filtered to collect the precipitate. The filtered precipitate was purified by recrystallization twice with methanol. The purified substance was dried at 50° C. for 6 hours.

Distilled water (800 ml) was heated to 60 to 70° C. to dissolve 15.9 g of the above reaction product. A solution of 4.92 g of basic salt of polyaluminum prepared in Reference Example 2 in 50 ml of distilled water was added to this solution of the reaction product. The mixture was stirred for 30 minutes at 60 to 70° C., and allowed to stand at the ambient temperature. A white precipitate produced was collected by filtration, washed thoroughly with distilled water, and recrystallized with methanol. The product thus produced was dried at 50° C. for 6 hours to obtain 16 g of a sample in a white powdery form.

EXAMPLE 3

Liquid paraffin (first grade, manufactured by Wako Pure Chemical Industries, Ltd.) was used as an oil component. Into this liquid paraffin 10% by weight of polyaluminum dicetyl phosphate prepared in Example 1, as a gelling agent, was dissolve at a high temperature. The solution was allowed to stand to cool down to the room temperature to obtain a transparent gel having thixotropic viscous characteristics. As comparative products, similar products were produced using aluminum tri(dicetyl)phosphate and metallic soaps; aluminum palmitate and aluminum stearate. The results are presented in Table 1.

TABLE 1

|  | Invention Product | Comparative Product | | |
|---|---|---|---|---|
|  |  | 1 | 2 | 3 |
| State of gel | Semi-solid | Oily Formed precipitate | Oily Formed precipitate | brittle solid |
| Transparency | Excellent |  |  | Good |

Comparative Product 1: aluminum palmitate
Comparative Product 2: aluminum stearate
Comparative Product 3: aluminum tri(dicetyl)phosphate As a result, it was demonstrated that while the product of this invention was a transparent, semi-solid thixotropic gel, the products prepared using metallic soaps produced precipitate while they were cooled, with no formation of a gel. In contrast, aluminum tri(dicetyl)phosphate produced a considerably solid gel. This gel, however, once broken down, must be heated to make it gelled again, and did not have thixotropic characteristics as seen in the product of this invention.

EXAMPLE 4

The melting point of polyaluminum dicetyl phosphate prepared in Example 1 was measured by means of SSC-5000; DSC200 manufactured by Seiko Electronic Co., Ltd. The gel strength of the same product was measured using n-hexadecane as an oily agent, after allowing the gel to stand at 20° C. for 2 days following gellation. A rheometer made by Fudo Industries Co., Ltd. was used.

Aluminum tri(dicetyl)phosphate and a metallic soap (aluminum distearate) were used for Comparative Products. The results are shown in Table 2.

TABLE 2

|  | Invention Product | Comparative product | |
|---|---|---|---|
| Gelling agent | Polyaluminum dicetyl-phosphate | Aluminum tri(dicetyl)-phosphate | Aluminum distearate |
| Melting point of the gelling agent (°C.) | 28.5 | 73 | 70 |
| Concentration of the gelling agent/n-hexadecane (wt %) | 8 | 8 | 8 |
| Gel strength (g/cm$^2$) | 8 | 500 | 475 |

The results of this test demonstrate that the gelling agent of this invention has a lower melting point, and because of this the gel produced using this gelling agent exhibits thixotropic, viscous characteristics. In contrast, aluminum tri(dicetyl)phosphate and aluminum distearate produced stiff gels.

EXAMPLE 5

Water-in-oil type moisture cream

Water-in-oil type moisture creams having formulations presented in Table 3 were prepared to compare their stability. The amounts of aluminum tri(dicetyl)-phosphate and aluminum distearate formulated to Comparative Products was 1% based on the amount of oil used, since formulating 10% or more of these compounds produced a hard, stiff gels, and did not produce creams. <Formulation>

TABLE 3

|     | Composition (%) | Inventive Product | Comparative Product 4 | 5 | 6 |
|-----|-----------------|-------------------|----|----|----|
| (1) | Gelling agent (Product of Example 1) | 4.4 | — | — | — |
| (1)' | Aluminum tri(dicetyl)-phosphate | — | 0.4 | — | — |
| (1)" | Aluminum distearate | — | — | 0.4 | — |
| (2) | Liquid paraffin | 40 | 40 | 40 | 40 |
| (3) | Water | 57 | 57 | 57 | 57 |
| (4) | Sorbitan sesquioleate | 3 | 3 | 3 | 3 |

<Preparation>

Component (1), (1)' or (1)", liquid paraffin (2), and sorbitan sesquioleate (4) were dissolved under heating at 70° C. After formation of oil gel, the product was emulsified into water-in-oil type emulsion. <Result>

Table 4 shows amounts of oil oozing out at 1 week after the emulsions were prepared.

TABLE 4

|                      | Amounts of oozed oil |
|----------------------|----------------------|
| Invention Product    | 0                    |
| Comparative Product 1 | 16                  |
| Comparative Product 2 | 15                  |
| Comparative Product 3 | 26                  |

Among the water-in-oil type emulsions, only the one produced by using the gelling agent of this invention exhibited an excellent stability, provided excellent gloss, and favorably adapted itself to the skin. In contrast, other products to which other additives were added could not exhibit the comparative stability and separation of the components began at 1 day after the preparation.

EXAMPLE 6

Water-in-oil type moisture cream

Water-in-oil type moisture creams having formulations presented in Table 3 were prepared to compare their stability. <Formulation>

TABLE 5

| Composition (%) | Inventive Product 1 | 2 | 3 | Comparative Product 7 | 8 | 9 |
|-----------------|----|-----|-----|----|------|----|
| (1) Gelling agent (Product of Example 1) | 2 | 1.5 | 0.3 | — | — | — |
| (2) Liquid paraffin | 13 | 9 | 2.7 | 15 | 10.5 | 3 |
| (3) Purified water | 80 | 85 | 95 | 80 | 85 | 95 |
| (4) Sorbitan sesquioleate | 5 | 4.5 | 2 | 5 | 4.5 | 2 |

<Preparation>

Water-in-oil type moisture creams were prepared according to a conventional method. As a result it was found that among systems holding 80 or 85% by weight of water, in the ones to which no gelling agent was added, separation occurred due to agglomeration of water atoms. In contrast, the systems to which the gelling agent of this invention was added maintained a stable state of gel. On the other hand, the composition containing 95% of water, without the gelling agent being added, the emulsion inverted into oil-in-water type and did not become creamy. In the composition to which the gelling agent of this invention was added, however, water was successfully held in oil to form a water-in-oil type emulsion, even though its content was 95%. This demonstrates that the compound of this invention can effectively prevent water molecules from becoming agglomerated and thus can be used as an emulsifier.

EXAMPLE 7

Oily foundation

Oil Foundation having formulations presented in Table 6 were prepared. Polyaluminum dicetyl phosphate prepared in Example 2 was used for Invention Product and aluminum distearate was used for Comparative Product. Outward appearances of the products were compared. To Invention Product 10%, based on the amount of oil, of polyaluminum dicetyl phosphate was added while to Comparative Product the amount of aluminum distearate added was 1% by weight based on oil, since the addition of 10% resulted in formation of a stiff, solid gel which was not suitable as a foundation.

TABLE 6

|     | Composition | Invention Product | Comparative Product |
|-----|-------------|-------------------|---------------------|
| (1) | Gelling agent (Product of Example 2) | 7.5 | — |
| (1)' | Aluminum distearate | — | 0.7 |
| (2) | Liquid paraffin | 30.7 | 37.5 |
| (3) | Lanolin | 12.0 | 12.0 |
| (4) | Isopropyl mirystate | 25.0 | 25.0 |
| (5) | Beeswax | 9.0 | 9.0 |
| (6) | Petrolatum | 8.0 | 8.0 |
| (7) | Titanium oxide | 5.0 | 5.0 |
| (8) | Red iron oxide | 1.0 | 1.0 |
| (9) | Yellow iron oxide | 1.0 | 1.0 |
| (10) | Black ion oxide | 0.4 | 0.4 |
| (11) | Perfume | 0.4 | 0.4 |

<Preparation>

The gelling agent (1) or (1)', and oil components (2), (3), and (4) were blended at 70 to 100° C. to dissolve and to obtain gels. After gellation, oily foundations were prepared according to a conventional method. <Results>

Comparison of oily foundations thus prepared revealed that the composition to which the invented gelling agent was added was more stable and oozed less oils. The composition did not produce cracks and color separation because of its excellent pigment dispersing capability.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent is:

1. A polyaluminum dialkyl phosphate which is prepared by the reaction of:

(A) a dialkyl phosphate represented by formula (I):

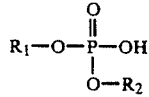

(I)

wherein $R_1$ and $R_2$ independently represent an alkyl group of a $C_{8-26}$ carbon atom content, or a salt thereof, and (B) a basic polyaluminum salt represented by formula (II):

$$Al_m(OH)_nX_l \cdot kH_2O \qquad (II)$$

wherein X represents an anion having a valency of x other than hydroxyl ion, m represents a positive integer satisfying the equation: $3m = n + xl$, and k represents 0 or a positive integer, in an aqueous medium in which the resulting polyaluminum dialkyl phosphate is insoluble.

* * * * *